United States Patent [19]

Strupczewski

[11] Patent Number: 4,524,074

[45] Date of Patent: Jun. 18, 1985

[54] 3-(4-PIPERIDINYL)-1,2-BENZISO-THIAZOLES

[75] Inventor: Joseph T. Strupczewski, Flemington, N.J.

[73] Assignee: Hoechst-Roussel Pharmaceuticals Inc., Somerville, N.J.

[21] Appl. No.: 602,780

[22] Filed: Apr. 23, 1984

Related U.S. Application Data

[62] Division of Ser. No. 499,583, May 31, 1983, Pat. No. 4,458,076.

[51] Int. Cl.³ .......................................... A61K 31/445
[52] U.S. Cl. ..................................................... 514/321
[58] Field of Search ........................................ 424/267

[56] References Cited

U.S. PATENT DOCUMENTS

| 4,104,388 | 8/1978 | Wade et al. | 424/250 |
| 4,140,693 | 2/1979 | Wade et al. | 424/250 |
| 4,147,698 | 4/1979 | Wade et al. | 424/270 |
| 4,148,798 | 4/1979 | Wade et al. | 424/270 |
| 4,166,910 | 9/1979 | Wade et al. | 544/212 |
| 4,352,811 | 10/1982 | Stupczewski et al. | 424/267 |

Primary Examiner—Stanley J. Friedman
Attorney, Agent, or Firm—Raymond R. Wittekind

[57] ABSTRACT

Novel 3-(4-piperidinyl)-1,2-benzisothiazoles, processes for the preparation thereof, and method of treating psychoses and alleviating pain employing compounds or compositions thereof are disclosed.

2 Claims, No Drawings

3-(4-PIPERIDINYL)-1,2-BENZISOTHIAZOLES

This is a division of application Ser. No. 499,583, filed May 31, 1983 now U.S. Pat. No. 4,458,076.

The present invention relates to 3-(4-piperidinyl)-1,2-benzisothiazoles. More particularly, the present invention relates to 3-(4-piperidinyl)-1,2-benzisothiazoles of formula 1

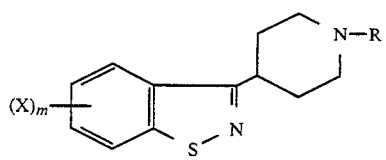

wherein R is hydrogen, loweralkyl, loweralkenyl, cycloalkylloweralkyl, phenylloweralkyl, hydroxy, diloweralkylaminoloweralkyl, cyano, cyanomethyl,

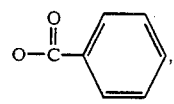

a group of the formula

wherein $R^1$ is hydrogen, loweralkyl or a group of the formula $OR^2$ wherein $R^2$ is phenyl or benzyl; a group of the formula

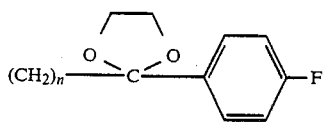

wherein n is 2 or 3; a group of the formula

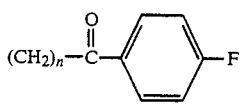

wherein n is 2 or 3; a group of the formula

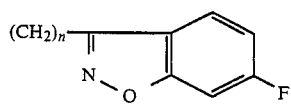

wherein n is 2 or 3; a group of the formula

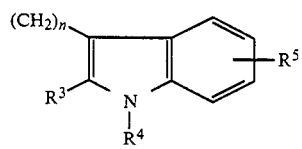

wherein $R^3$ and $R^4$ are each independently hydrogen or loweralkyl, $R^5$ is hydrogen, halogen or loweralkyl, and n is 2 or 3; a group of the formula

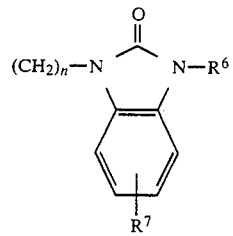

wherein $R^6$ is hydrogen or loweralkyl, $R^7$ is hydrogen, halogen or loweralkyl, and n is 2 or 3; or a group of the formula

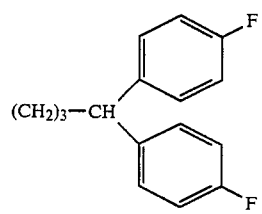

X is hydrogen, halogen, loweralkyl, loweralkoxy or hydroxy; and m is 1 or 2; the optical antipodes thereof; or pharmaceutically acceptable acid addition salts thereof, which are useful for treating psychoses alone or in combination with inert psychoses treating adjuvants.

Subgeneric to the 3-(4-piperidinyl)-1,2-benzisothiazoles of the present invention are compounds wherein:

(a) R is hydrogen, loweralkyl, loweralkenyl or cycloalkylloweralkyl;
(b) R is phenylloweralkyl;
(c) R is hydroxy or

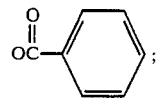

(d) R is diloweralkylaminoloweralkyl;
(e) R is cyano or cyanomethyl; and
(f) R is a group of the formula

wherein $R^1$ is hydrogen, loweralkyl or a group of the formula $OR^2$ wherein $R^2$ is phenyl or benzyl.

Preferred 3-(4-piperidinyl)-1,2-benzisothiazoles of the present invention are those compounds wherein R is:

(a) A group of the formula

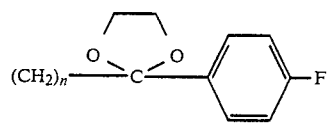

wherein n is as above;

(b) A group of the formula

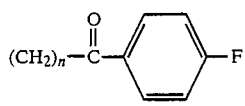

wherein n is as above;
(c) A group of the formula

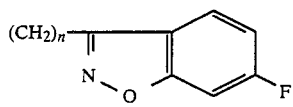

wherein n is as above;
(d) A group of the formula

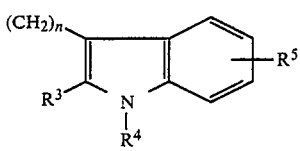

wherein $R^3$, $R^4$, $R^5$ and n are as above;
(e) A group of the formula

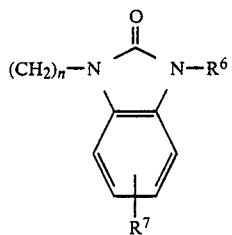

wherein $R^6$, $R^7$ and n are as above; and
(f) A group of the formula

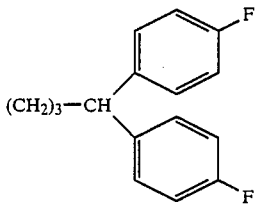

Most preferred 3-(4-piperidinyl)-1,2-benzisothiazoles of the present invention are those compounds wherein R is loweralkyl.

As used through the specification and appended claims, the term "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 2-pentyl, 3-hexyl, 4-heptyl, 2-octyl, 3-nonyl, 4-decyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, 2-methyloctoxy, octoxy, decoxy and the like; the term "alkanol" refers to a compounds formed by a combination of an alkyl group and a hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, octanoic acid, decanoic acid and the like; the term "halogen" refers to a member of the family consisting of fluorine, bromine or iodine. The term "alkanone" refers to a compound formed by the combination of a carbonyl group and two alkyl groups. Examples of alkanones are acetone, 2-butanone, 3-pentanone, 3-hexanone and the like. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The present invention comprehends all optical isomers and racemic forms thereof and all geometric isomers of the compounds disclosed and claimed herein. The formulas of the compounds shown herein are intended to encompass all possible geometric and optical isomers of the compounds so depicted.

The novel 3-(4-piperidinyl)-1,2-benzisothiazoles 1 of the present invention are synthesized by the process illustrated in Reaction Schemes A and B.

To prepare the parent system, i.e., a 3-(4-piperidinyl)-1,2-benzisothiazole 7 wherein X and m are as herinbeforedescribed, a 4-(2-fluorobenzoyl-1-alkylpiperidine 2 wherein $R^8$ is alkyl, the synthesis of which is described in U.S. patent application Ser. No. 319,871, filed Nov. 11, 1981, now U.S. Pat. No. 4,355,037, granted Oct. 19, 1982, is cyclized to a 3-(1-alkyl-4-piperidinyl)-1,2-benzoisothiazole 3 wherein $R^8$ is alkyl, which in turn is cyanated to a 3-(1-cyano-4-piperidinyl)-1,2-benzisothiazole 6 and hydrolyzed to a compound of formula 7.

The cyclization of benzoylpiperidine 2 to benzisothiazole 3 is conveniently performed by treating 2 with sulfur in an alkanol saturated with ammonia at an elevated temperature of about 75° to about 150° C. in a suitable reaction vessel, e.g., an autoclave. Among alkanols there may be mentioned, in addition to those hereinbeforedefined, glycol monoalkyl ethers such an ethylene glycol monomethyl ether, 1,2-propylene glycol 1-monoethyl ether, diethylene glycol monomethyl ether and the like. Ethylene glycol monomethyl ether is the preferred alkanol. A reaction temperature of about 130° C. is also preferred.

The cyanation of a 1-alkylpiperidine 3 to a 1-cyanopiperidine 6 is accomplished by contacting 3 with a cyanogen halide 4 such as cyanogen bromide or cyanogen chloride, preferably cyanogen bromide, in a halocarbon such as dichloromethane, trichloromethane or dichloroethane, preferably trichloromethane, in the presence of an acid scavenger such as sodium or potassium carbonate or sodium or potassium bicarbonate, preferably potassium carbonate, to afford an alkyl-cyanopiperidinium salt 5, which loses the elements of an alkylhalide ($R^8$Hal) to form a 1-cyano derivative 6. The reaction proceeds readily at moderate temperatures. To facilitate the conversion, however, an elevated temperature, i.e., the reflux temperature of the system, is employed. A promotor such as potassium iodide may be employed to facilitate the conversion.

The hydrolysis of a 1-cyanopiperidine 6 to a 3-(4-piperidinyl)-1,2-benzisothiazole 7 is conducted by conventional methods involving acidic or basic reaction conditions as described in R. B. Wagner and H. P. Zook, "Synthetic Organic Chemistry", John Wiley and Sons, Inc., New York, N. Y., page 680 and references cited therein. For example, treatment of 3-(1-cyano-4-piperidinyl)-1,2-benzisothiazole 6 wherein X is hydrogen with 25% sulfuric acid at the reflux temperature of the reaction mixture affords 7.

Derivatives of the parent system, i.e., derivatives of the 3-(4-piperidinyl)-1,2-benzisothiazole system, are prepared from a nitrogen unsubstituted compound 7 by the processes outlined in Reaction Scheme B.

To prepare a 3-(1-alkenyl-4-piperidinyl)-1,2-benzisothiazole 1 wherein R is alkenyl, a 3-(1-unsubstituted-4-piperidinyl)-1,2-benzisothiazole 7 may be contacted with an alkenyl halide in a suitable solvent in the presence of an acid acceptor. Suitable solvents include polar aprotic substances such a dimethylacetamide, dimethylformamide and hexamethylphosphoramide. Suitable acid acceptors include alkali carbonates and alkali bicarbonates such as potassium carbonate and sodium bicarbonate. Potassium iodide and elevated temperatures within the range of 75°-100° C. may be employed to promote the alkenylation.

To synthesize a 3-(1-phenylalkyl-4-piperidinyl)-1-2,-benzisothiazole 1 wherein R is phenylalkyl or a 3-(1-cycloalkylalkyl-4-piperidinyl)-1-2,-benzisothiazole 1 wherein R is cycloalkylalkyl, a 1-unsubstituted compound 7 is treated, respectively, with a phenylalkyl halide or a cycloalkylalkyl halide in a polar aprotic solvent such as dimethylacetamide, dimethylformamide and hexamethylphosphoramide, in the presence of an acid scavenger such as sodium or potassium carbonate or bicarbonate. A promotor such as potassium iodide may be used and the reaction may be conducted at an elevated temperature of 50°-100° C. to facilitate the conversion. Potassium carbonate in dimethylformamide at 60°-90° C. are the preferred reaction conditions.

To introduce the dialkylaminoalkyl group into the 1-unsubstituted piperidinylbenzisothiazole 7, i.e., to prepare a 3-(1-dialkylaminoalkyl-4-piperidinyl)-1,2-benzisothiazole 1 wherein R is dialkylaminoalkyl, one may treat a piperidinylbenzisothiazole 7 with a dialkylaminoalkyl halide in an alkanol, for example, methanol, ethanol, 2-propanol, 1-butanol and the like, n-butanol being preferred, in the presence of an acid acceptor such as an alkali carbonate (potassium carbonate) or bicarbonate (sodium bicarbonate). As in similar alkylations, a promotor such as potassium iodide and elevated temperatures, for example, the reflux temperature of the reaction system, may be used to facilitate the reaction.

To prepare a 3-(1-hydroxy-4-piperidinyl)-1,2-benzisothiazole 9, a 1-unsubstituted compound 7 is treated with benzoyl peroxide in an aromatic solvent such as benzene, toluene or xylene, benzene being preferred, in the presence of a base such as an alkali metal carbonate or bicarbonate, for example, potassium carbonate or sodium bicarbonate, potassium carbonate being preferred, to yield a 3-(1-benzoyloxy-4-piperidinyl)-1,2-benzisothiazole 8, which is hydrolyzed by methods known per se such as by an alkali hydroxide (sodium hydroxide) in an aqueous alkanol (aqueous ethanol) to provide the 1-hydroxy compound 9. Neither the oxidation nor hydrolysis temperatures are narrowly critical. At about ambient temperature, the oxidation proceeds at a reasonable rate, and at the reflux temperature of the reaction system, the hydrolysis also proceeds at a convenient rate.

To synthesize a 3-(1-cyanomethyl-4-piperidinyl)-1,2-benzisothiazole 10, a 1-unsubstituted piperidine 7 is contacted with a haloacetonitrile such as chloro- or bromoacetonitrile, preferably chloroacetonitrile, in a polar aprotic solvent such as dimethylformamide, dimethylacetamide or hexamethylphosphoramide, preferably dimethylformamide, in the presence of an acid acceptor such as potassium or sodium bicarbonate or potassium or sodium carbonate, preferrably potassium carbonate, and a promotor such as potassium iodide. To assure completion of the conversion, an elevated temperature within the range of about 50° to 100° C. may be employed. A temperature within the range of about 80° to 85° C. is preferred.

The introduction of an acyl group, i.e. an acyl group of the formula

wherein $R^1$ is hydrogen or alkyl into a 3-(4-piperidinyl)-1,2-benzisothiazole 7 is affected by treating the piperidine 7 with an anhydride by methods well-known in the art. For example, treatment of 3-(4-piperidinyl)-1,2-benzisothiazole 7 where X is hydrogen with acetic anhydride, in the presence or absence of a co-solvent, such as acetic acid, at ambient temperature yields 11 wherein $R^1$ is methyl. To prepare the N-formyl derivative 11 wherein $R^1$ is hydrogen, acetic-formic acid anhydride, prepared from acetic anhydride and formic acid, is employed. In this case, it is preferable to utilize the mixed anhydride, acetic-formic acid anhydride, in situ, and a slightly reduced temperature within the range of about 0° to about 25° C. To introduce an acyl group, i.e., an acyl group of the formula

wherein $R^1$ is a group of the formula $OR^2$ wherein $R^2$ is phenyl or benzyl, one treats a piperdine 7 with a benzyl or phenyl haloformate, for example, benzyl chloroformate or benzyl bromoformate, or phenyl chloro- or bromoformate, respectively, in a halocarbon such as dichloromethane, chloroform or the like, in the presence of an acid scavenger such as an alkali carbonate (potassium carbonate) or alkali bicarbonate (sodium bicarbonate). Benzyl and phenyl chloroformate are the preferred reagents. Dichloromethane containing sodium bicarbonate is the preferred reaction medium.

To prepare 3-(4-piperidinyl)-1,2-benzisothiazoles having a 4-fluorobenzoylalkyl group bound to the nitrogen atom of the piperidine ring, a 3-(1-unsubstituted-4-piperidinyl)-1,2-benzisothiazole 7, is condensed with a 4-fluorobenzoylalkyl halide ethylene glycol ketal of formula 12

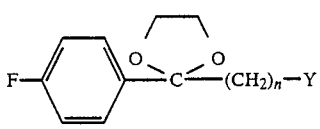

wherein Y is chloro or bromo and n is 2 or 3, to afford a 3-[1-(4-fluorobenzoylalkyl)-4-piperidinyl]-1,2-benzisothiazole ethylene ketal 1 wherein R is

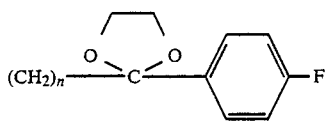

wherein n is as above, which is hydrolized to a 3-[1-(4-fluorobenzoylalkyl)-4-piperidiyl]-1,2-benzisothiazole 1 wherein R is

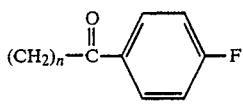

wherein n is as above.

The condensation is readily performed by treating an N-unsubstituted piperidine 7 with a halide 12 in the presence of an acid acceptor, a displacement promotor and a suitable solvent. Among acid acceptors, there may be mentioned alkali metal carbonates and alkali metal bicarbonates such as, for example, sodium and potassium carbonate and sodium and potassium bicarbonate. Sodium bicarbonate and potassium carbonate are preferred. Among displacement promoters, there may be mentioned alkali metal halides such as, for example, sodium and potassium iodide, and sodium and potassium bromide. Potassium iodide is preferred. Among suitable solvents, there may be mentioned polar aprotic substances such as dimethylformamide, dimethylacetamide and hexamethylphosphoramide. Dimethylformamide is preferred. The temperature at which the condensation is conducted is not narrowly critical. It is desirable, however, to perform the reaction at a temperature within the range of about 50° to about 130° C. to assure a reasonable rate of conversion. A reaction temperature within the range of about 80° to 110° C. is preferred.

The preferred 4-fluorobenzoylalkyl halide ethylene glycol ketal of formula 12 is a compound wherein Y is chloro.

The hydrolysis of the ethylene ketal moiety of a 3-[1-(4-fluorobenzoylalkyl)-4-piperidinyl]-1,2-benzisothiazole of formula 1 is conveniently accomplished by conventional methods involving, for example, the interaction of the ketal with a mineral acid such as hydrochloric acid, in an alkanol such as methanol, at ambient temperature, or an elevated temperature such as the reflux temperature of the reaction system.

Similarly, to prepare a 3-[1-(6-fluoro-1,2-benzisoxazol-3-alkyl)-4-piperidinyl]-1,2-benzisothiazole, a compound of formula 1 wherein R is

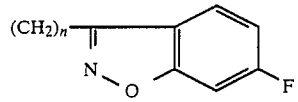

wherein n is as above, a 3-(1-unsubstituted-4-piperidinyl)-1,2-benzisothiazole 7 is condensed with a 3-(ω-haloalkyl)-6-fluoro-1,2-benzisoxazole of formula 13

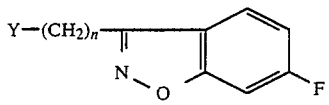

wherein Y is bromo or chloro, and n is as above, preferably a haloalkylbenzisoxazole of formula 13 wherein Y is chloro, in the presence of an alkali metal carbonate or alkali metal bicarbonate, preferably potassium carbonate or sodium bicarbonate, as an acid acceptor, and an alkali metal halide, preferably potassium iodide, as a reaction promotor, in an aprotic polar solvent, preferably dimethylformamide, at a condensation temperature, preferably within the range of about 80° to about 100° C.

To introduce the indol-3-ylalkyl function, i.e., to fabricate a 3-{ω-[4-(1,2-benzisothiazol-3-yl)piperidinyl]-alkyl}indole of formula 1 wherein R is a group of the formula

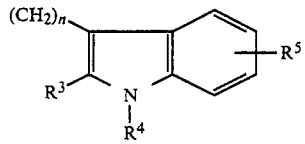

wherein $R^3$, $R^4$, $R^5$ and n are as above, one treats a 3-(1-unsubstituted-4-piperidinyl)-1,2-benzisothiazole 7 with a 3-(phenylsulfonylalkyl)indole of formula 14

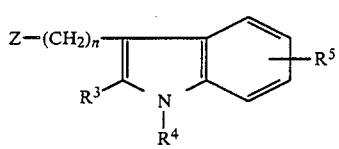

wherein Z is a group of the formula

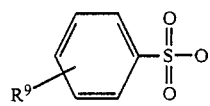

wherein $R^9$ is hydrogen or alkyl and $R^3$, $R^4$, $R^5$ and n are as above.

The reaction involving the displacement of the phenylsulfonyl group of 14 is accomplished by treating an N-unsubstituted piperidine 7 with a sulfonyl compound 14 in an aprotic polar sovent, such as dimethylformamide, dimethylacetamide and hexamethylphosphoramide, or in an alkanone such as acetone, 2-butanone, 3-pentanone and the like, dimethylformamide and 2-butanone being preferred, in the presence of an acid scavenger such as an alkali metal carbonate (sodium or potassium carbonate) or alkali metal bicarbonate (sodium or potassium bicarbonate), potassium carbonate and sodium bicarbonate being preferred, at a temperature of about 70° to about 100° C., preferably a temperature of 90° C., when an aprotic polar solvent is used, and at about the reflux temperature of the reaction system when an alkanol is employed as the solvent.

A (phenylsulfonylalkyl)indole, i.e., a compound of formula 14 wherein $R^9$ is hydrogen, is the preferred reaction partner.

To prepare 3-(4-piperidinyl)-1,2-benzisothiazoles characterized by the presence of a 1,3-dihydro-2-oxo-2H-benzimidazol-1-yl-alkyl group, i.e., a compound of formula 1 wherein R is

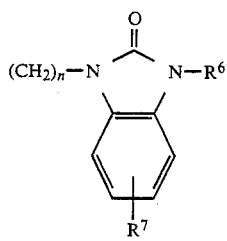

wherein $R_6$, $R_7$ and n are as above, an N-unsubstituted piperidine 7 is contacted with a 1-(ω-haloalkyl)-1,3-dihydro-2H-benzimidazol-2-one of formula 15

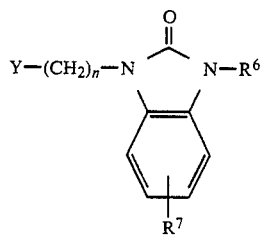

wherein Y is bromo or chloro, $R^6$, $R^7$ and n are as above in the presence of a base in an appropriate solvent. Bases include alkali metal carbonates such as, for example, sodium carbonate and potassium carbonate, and alkali metal bicarbonates such as, for example sodium bicarbonate and potassium bicarbonate. Sodium and potassium carbonates are preferred. Appropriate solvents include alkanones, for example, acetone, 2-butanone and 4-methyl-2-pentanone and the like. 4-Methyl-2-pentanone is preferred. To facilitate the displacement reaction, a promoter, for example, an alkali metal halide such as sodium or potassium iodide, is employed. While the reaction proceeds readily at moderate temperature, it may be carried out at elevated temperatures, such as the reflux temperature of the reaction system to assure a reasonable rate of conversion.

A 1-(3-chloroalkyl-1,3-dihydro-2H-benzimidazole-2-one, i.e., a compound of formula 15 wherein Y is chloro, is a preferred reaction substrate.

In a like manner, to incorporate the 4,4-bis-(4-fluorophenyl)-1-butyl group into a 3-(1-unsubstituted-4-piperidinyl)-1,2-benzisothiazole, i.e., to elaborate a compound of formula 1 wherein R is

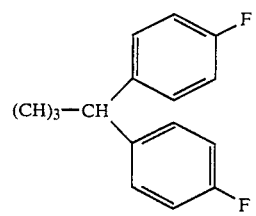

one treats a 3-(1-unsubstituted-4-piperidinyl)-1,2-benzisothiazole 7 with a 4,4-bis-(4-fluorophenyl)butylhalide of formula

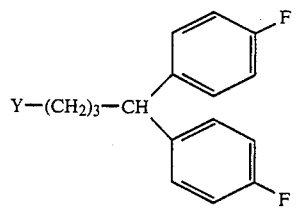

wherein Y is chloro or bromo is an aprotic polar solvent such as dimethylformamide, dimethylacetamide and hexamethylphosphoramide, in the presence of an acid acceptor such as an alkali metal carbonate, for example, sodium or potassium carbonate or an alkali metal bicarbonate, for example, sodium or potassium bicarbonate. Dimethylformamide is the preferred solvent, and potassium carbonate and sodium bicarbonate are the preferred acid acceptors. A displacement promoter such as an alkali metal halide, for example, sodium or potassium iodide may be employed to facilitate the reaction. Elevated temperatures within the range of about 50° to about 120° C. may also be employed to facilitate the reaction, even though the reaction temperature is not critical.

4-Fluorobenzoylalkylhalide ethylene glycol ketals of formula 12, the substrates for the preparation of 3-[1-(4-fluorobenzoylalkyl)-4-piperidinyl]-1,2-benzisothiazole ethylene ketals of formula 1 and 3-[1-(4-fluorobenzoylalkyl)-4-piperidinyl]-1,2-benzisothiazoles of formula 1, is prepared from commercially available γ-halo-4-fluorophenones of formula 17

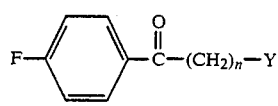

wherein Y is chloro or bromo and n is 2 or 3 by methods well known in the art. For example, treatment of γ-chloro-4-fluorobutyrophenone with ethylene glycol in the presence of a mineral acid such as sulfuric acid by the method described in R. B. Wagner and H. D. Zook (see "Synthetic Organic Chemistry", John Wiley and Sons, Inc., New York, N.Y., 1953, pages 262 and 263) furnishes γ-chloro-4-fluorobutyrophenone ethylene ketal.

3-(3-Haloalkyl)-6-fluoro-1,2-benzisoxazoles of formula 13, one of the starting materials for the synthesis of 3-[1-(6-fluoro-1,2-benzisoxazole-3-alkyl)-4-piperidinyl]-1,2-benzisothiazoles of formula 1, is obtained by following the preparative procedures disclosed in U.S. patent application Ser. No. 257,698, filed Apr. 27, 1981.

3-(Phenylsulfonylalkyl)indoles and 3-(alkylphenylsufonylalkyl)indoles of formula 14, precursors for the preparation of 3-{3-[4-(1,2-benzisothiazol-3-yl)piperidinyl]alkyl}indoles of formula 1, are constructed by conventional processes, involving, for example, the interaction of a hydrazine of formula 18 wherein $R^4$ is hydrogen or alkyl and $R^5$ is hydrogen, halogen or alkyl, with a ketoester or aldehydoester of formula 19, wherein $R^3$ is hydrogen or alkyl and n is 2 or 3 under the condition of the Fischer indole synthesis (R. B. Wagner and H. D. Zook, ibid., page 844) to form an indole-3-yl-alkanoic acid ester of formula 20 wherein $R^3$, $R^4$, $R^5$ and n are as above and $R^{10}$ is alkyl, followed by reduction of the ester group of the compound of formula 20 with lithium aluminum hydride to afford an indol-3-yl-alkanol of formula 21 wherein $R^3$, $R^4$, $R^5$ and n are as above (R. B. Wagner and H. D. Zook, ibid., page 155), which, in turn, is converted to the sulfonyl derivative 22 by means of a sulfonylhalide of formula 23 wherein $R^{11}$ is phenyl or alkylphenyl and V is chloro or bromo (R. D. Wagner and H. D. Zook, ibid., page 823). (See Scheme C).

1-(3-Haloalkyl)-1,3-dihydro-2H-benzimidazol-2-ones of formula 17, reactants for the synthesis of 3-{1-[1,3-dihydro-2-oxo-2H-benzimidazol-1-ylalkyl]-4-piperidinyl}-1,2-benzisothiazoles of formula 1, are prepared by the processes described by J. Davall and D. H. Lang in J. Chem. Soc., 314 (1960) and by J. Vandenmark, et al., in U.S. Pat. No. 4,066,772, granted Jan. 3, 1976.

Precursors for the elaboration of 3-{1-[4,4-bis(4-fluorophenyl)-1-alkyl]-4-piperidinyl}-1,2-benzisothiazoles 1, namely, halo-1,1-bis(4-fluorophenyl)alkanes of formula 16, are prepared according to the procedure disclosed by P. A. Janssen in U.S. Pat. No. 3,238,216, granted Mar. 1, 1966; Chem. Abs., 65, 8922f (1966). For example, as depicted below, ethyl cyclopropyl carboxylate 24 is treated with the Grignard reagent of 4-fluorobromobenzene 25 to afford the carbinol 26 which is treated with a thionyl halide to furnish a butenyl halide 27. Catalytic hydrogenation of butenyl halide 27 yields 1,1-bis(4-fluorophenyl)butyl halide 28. See Scheme D).

The 3-(4-piperidinyl)-1,2-benzisothiazoles of the present invention are useful for treating psychoses by virtue of their ability to elicit an antipsychotic response in mammals.

Antipsychotic activity is determined in the climbing mice assay by a method similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subject for 30 minutes. Compounds to be tested for neuroleptic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice with: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apormorphine will be discarded.

With full-developed apomorphine climbing, the animals are hanging on to the cage walls, rather motionless, over longer periods of time. By contrast, climbs due to mere motor stimuation usually only last a few seconds.

The climbing scores are individually totaled (maximal score: 6 per mouse over 3 readings) and the total score of the control group (vehicle intraperitoneally—apomorphine subcutaneously (is set to 100%). $ED_{50}$ values with 95% confidence limits, calculated by a Linear Regression Analysis of some of the instant 4-(piperidinyl)-1,2-benzisothiazoles as well as standard neuroleptics, are presented in Table 1.

TABLE 1

| COMPOUND | ANTIPSYCHOTIC ACTIVITY ($ED_{50}$ mg/kg) |
|---|---|
| 3-{1-(cyclopropylmethyl)-4-piperidinyl}-1,2-benzisothiazole | 5.8 |
| 3-{1-[phenethyl]-4-piperidinyl}-1,2-benzisothiazole | 7.0 |
| 3-[1-(6-fluoro-1,2-benzisoxazole-3-propyl)-4-piperidinyl]-1,2-benzisothiazole | 0.17 |
| 3-[1-(1,3-dihydro-2-oxo-2H—benzimidazol-1-ylpropyl)-4-piperidinyl]-1,2-benzisothiazole | 0.32 |
| 3-{1-[4,4-bis(4-fluorophenyl)-1-butyl]-4-piperidinyl}-1,2-benzisothiazole | 3.3 |
| 3-{[-4-(1,2-benzisothiazole-3-yl)piperidinyl]propyl}-2-methyl indole | 0.17 |
| haloperidol (standard) | 0.11 |
| sulpiride (standard) | 14.5 |

Antipsychotic response is achieved when the present 3-(4-piperidinyl)-1,2-benzisothiazoles are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

3-(4-piperidinyl)-1,2-benzisothiazoles of the present invention are useful as analgetics due to their ability to alleviate pain in mammals. The analgetic utility is demonstrated in the phenyl-p-quinone writhing assay in mice, a standard assay for analgesia [Proc. Soc. Exptl. Biol. Med., 95, 729 (1957)]. Thus, for instance, the subcutaneous dose effecting an approximately 50% inhibition of writhing ($ED_{50}$) in mice produced in this assay is as shown in Table 2.

TABLE 2

| COMPOUND | ANALGETIC ACTIVITY (ED$_{50}$ mg/kg) |
| --- | --- |
| 3-(1-methyl-4-piperidinyl)-1,2-benzisothiazole | 0.73 |
| 3-(4-piperidinyl)-1,2-benzisothiazole | 2.1 |
| 3-{1-(cyclopropylmethyl)-4-piperidinyl}-1,2-benzisothiazole | 0.07 |
| 3-{1-[phenethyl]-4-piperidinyl}-1,2-benzisothiazole | 0.2 |
| 3-[1-(6-fluoro-1,2-benzisoxazol-3-propyl)-4-piperidinyl]-1,2-benzisothiazole | 0.30 |
| propoxyphene (standard) | 3.9 |
| pentazocine (standard) | 1.3 |

Analgesia production is achieved when the present 3-(4-piperidinyl)-1,2-benzisothiazoles are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Compounds of the invention also include:

(a) 4-chloro-3-[1-(1-propenyl)-4-piperidinyl]-1,2-benzisothiazole;
(b) 3-[1-(diethylaminoethyl)-4-piperidinyl]-5-methyl-1,2-benzisothiazole;
(c) 3-[1-(cyanomethyl)-4-piperidinyl]-6-methoxy-1,2-benzisothiazole;
(d) 7-hydroxy-3-(1-hydroxy-4-piperidinyl)-1,2-benzisothiazole;
(e) 5,6-dichloro-3-(1-formyl-4-piperidinyl)-1,2-benzisothiazole;
(f) 3-(1-acetyl-4-piperidinyl)-1,2-benzisothiazole;
(g) 4-(1,2-benzisothiazol-3-yl)-1-piperidine carboxylic acid phenyl ester;
(h) 4-(1,2-benzisothiazol-3-yl)-1-piperidine carboxylic acid benzyl ester;
(i) 3-[1-(4-fluorobenzoylpropyl)-4-piperidinyl]-1,2-benzisothiazole; and
(j) 3-[1-(4-fluorobenzoylpropyl)-4-piperidinyl]-1,2-benzisothiazole ethylene ketal.

Effective amounts of the compounds of the present invention may be administered to a subject by any one of the several methods, for example, orally as in capsules or tablets, parenterally in the form of sterile solutions or suspensions, and in some cases intravenously in the form of sterile solutions. The 3-(4-piperidinyl)-1,2-benzisothiazoles of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purposes of oral therapeutic administration, the aforesaid compounds may be incorporated with an excipient and used in the form of tablets, troches, capsules, elixirs, suspension, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of the active compound.

The tablets, pills, capsules, troches and the like may also contain the following ingredients: a binder such as microcrystalline cellulose, gum tragancanth or gelatine; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parentereal preparation can be enclosed in ampules, disposable syringes or multiple dose vials made of glass or plastic.

REACTION SCHEME A
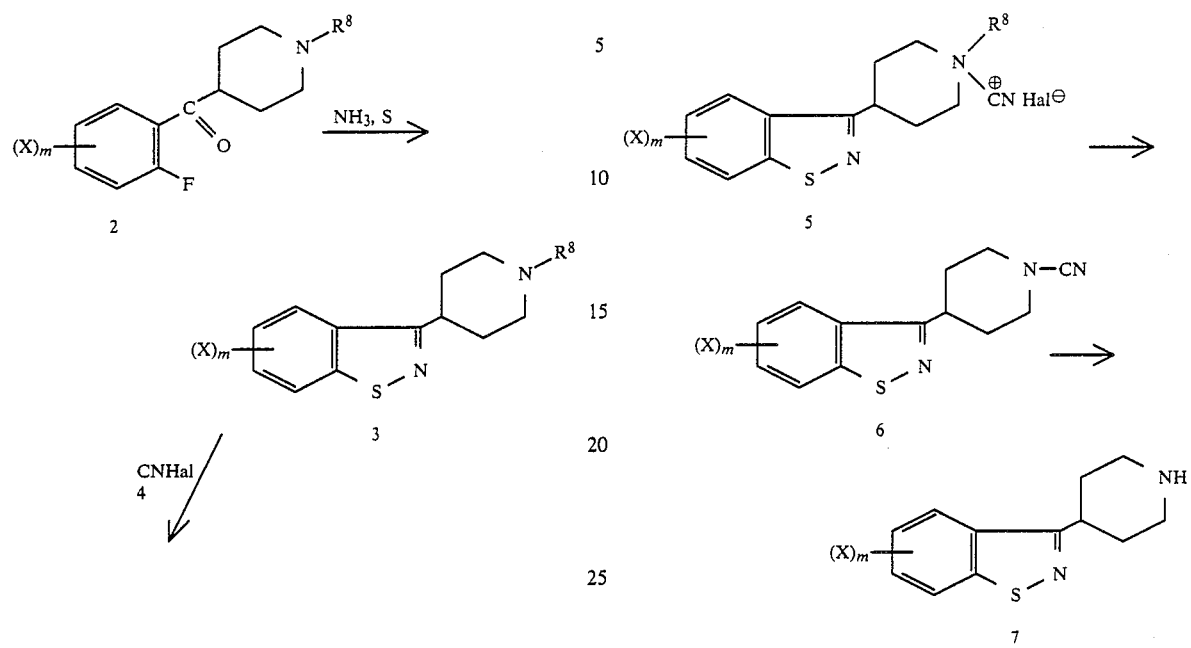
REACTION SCHEME B
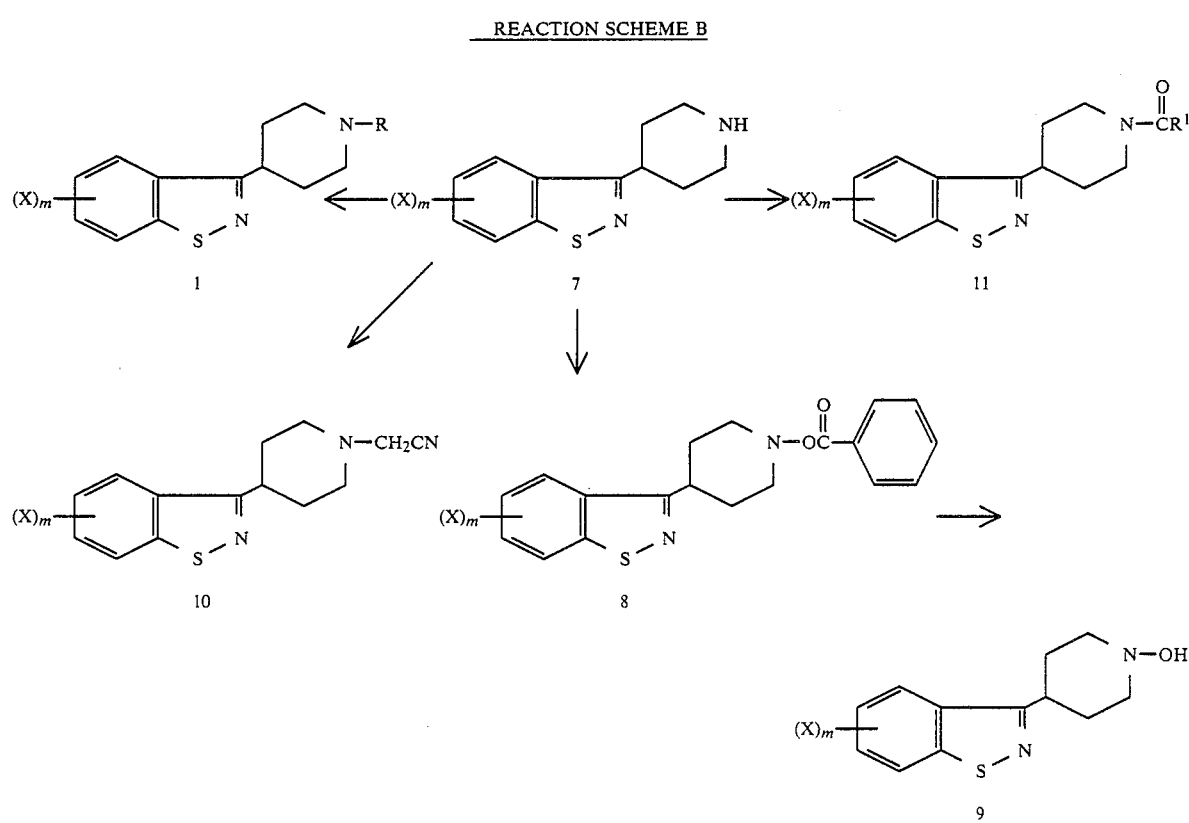

REACTION SCHEME C

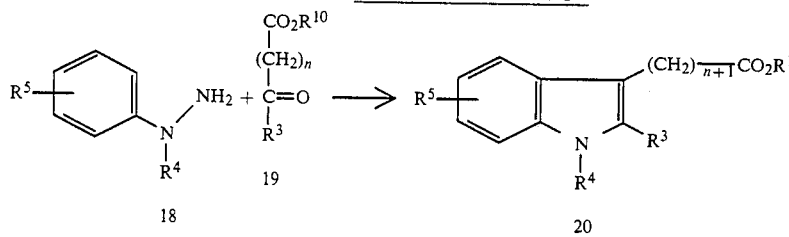

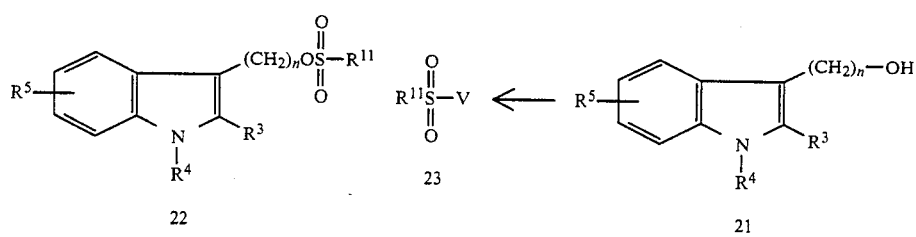

REACTION SCHEME D

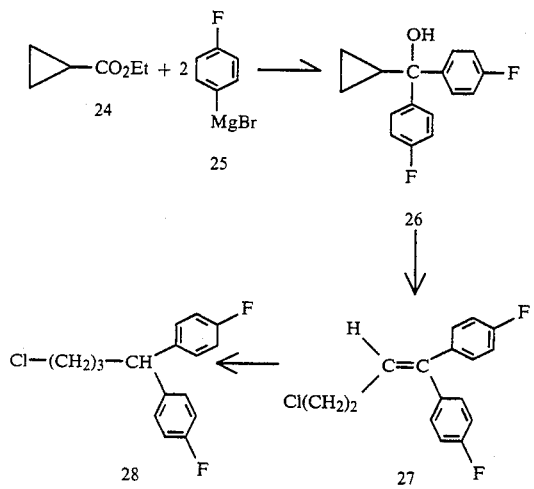

The following examples are for illustrative purposes only and are not to be construed as limiting the invention. All temperatures are given in degrees Centrigrade (°C.).

EXAMPLE 1

4-(2-Fluorobenzoyl)-1-methylpiperidine hydrochloride

To a suspension of 7.6 of magnesium turnings in 25 ml of tetrahydrofuran was added a few drops of ethyl bromide, with stirring under nitrogen. After the reaction began approximately 50.0 g of N-methyl-4-chloropiperidine in 125 ml of tetrahydrofuran was added dropwise at a rate such that moderate reflux was maintained. The reaction mixture was heated under reflux for an additional hour. A solution of 37.2 g of 2-fluorobenzonitrile in 30 ml of tetrahydrofuran was added dropwise. After completion of the addition, the reaction mixture was heated under reflux for two hrs and stirred overnight at room temperature. The reaction mixture was poured into a solution of 85 g of ammonium chloride in 1200 ml of ice water and heated on a steam bath for 3 hrs. The mixture was cooled, extracted with benzene (3×250 ml) and dried over anhydrous sodium sulfate. Removal of the solvent under reduced pressure gave an oil. A 1.0 g-portion of the oil was dissolved in ether and a solution of ethereal hydrogen chloride was added. The precipitate was collected, dried and twice recrystallized from ethanol-ether to give 0.5 g (42%) of product as crystals, mp 167°–169°.

Analysis: Calculated for $C_{13}H_{17}ClFNO$: 60.58%C: 6.65%H: 5.43%N: 7.37%F; Found: 60.30%C: 6.78%H: 5.43N: 7.59%F.

EXAMPLE 2

3-(1-Methyl-4-piperidinyl)-1,2-benzisothiazole hydrobromide

An autoclave was charged with 1.8 g of sulfur, 10.0 g of 4-(2-fluorobenzoyl)-1-methylpiperidine, and 40 ml of an ammonia saturated ethylene glycol monomethyl ether solution. The reaction mixture was heated at 130° for 13 hrs, with stirring. The mixture was cooled, filtered, and the filtrate was poured into water. The aqueous mixture was extracted with ether. The ether extract was washed with water and brine, dried over anhydrous magnesium sulfate, and the ether evaporated under reduced pressure to give an oil. The oil was dissolved in anhydrous ether and gaseous hydrogen bromide was added to precipitate the salt. Recrystallization from ethanol (twice), yielded 3.5 g (23.7%) of product, mp 244°–246°.

Analysis: Calculated for $C_{13}H_{16}N_2S.HBr$: 49.84%C: 5.15%H: 8.94%N; Found: 49.77%C: 5.31%H: 8.75%N.

EXAMPLE 3

3-(1-Cyano-4-piperidinyl)-1,2-benzisothiazole

To a stirred mixture of 5.9 g of cyanogen bromide, 8.6 g of potassium carbonate, and 80 ml of chloroform was added, dropwise, 11.0 g of 3-(2-methyl-4-piperidinyl)-1,2-benzisothiazole, in 30 ml of chloroform. The mixture was stirred under reflux for 4 hrs, cooled, filtered and the filtrate was concentrated in vacuo to a solid. The solid was triturated with hexane and recrystallized from methanol-water (twice) to yield 4.5 g (36%) of product, mp 118°–120°.

Analysis: Calculated for $C_{13}H_{13}N_3S$: 64.17%C: 5.38%H: 17.27%N; Found: 63.94%C: 5.35%H: 17.37%N.

EXAMPLE 4

3-(4-Piperidinyl)-1,2-benzoisthiazole hydrochloride

A mixture of 2.0 g of 3-(1-cyano-4-piperidyl)-1,2-benzisothiazole and 20 ml of 25% aqueous sulfuric acid was stirred under reflux for 16 hrs. After stirring at ambient temperature for about 34 hr, the reaction mixture was poured into water and the solution made basic with aqueous sodium hydroxide solution. The basic mixture was extracted with dichloromethane. The dichloromethane extract was washed with water, dried over anhydrous magnesium sulfate and the solvent removed in vacuo to yield an oil. The oil was dissolved in absolute ether and saturated ether-hydrogen chloride solution was added to precipitate the salt. Recrystallization from ethanol-ether gave 0.9 g (42.8%) of product, mp 269°–270°.

Analysis: Calculated for $C_{12}H_{14}H_2S.HCl$: 56.36%C: 5.91%H; 10.96%N; Found: 56.49%C: 5.81%H: 10.70%N.

EXAMPLE 5

3-{1-(cyclopropylmethyl)-4-piperidinyl}-1,2-benzisothiazole hydrobromide

A stirred mixture of 5.0 g of 3-(4-piperidinyl)-1,2-benzisothiazole, 2.30 g of cyclopropylmethyl chloride, 7.95 g of potassium carbonate, 0.25 g of potassium iodide and 90 ml of dimethylformamide was heated at 90° for 20 hrs. The reaction mixture was poured into water and extracted with ethyl acetate. The organic extract was dried over anhydrous magnesium sulfate and the solvent was removed in vacuo to yield an oil. The oil was dissolved in ether and saturated hydrogen bromide/ether solution was added dropwise to precipitate the salt. The salt was recrystallized two times from ethyl acetate/ethanol to yield 2.0 g (25%) of product, mp 214°–216°.

Analysis: Calculated for $C_{16}H_{20}N_2S.HBr$: 54.39%C: 5.67%H: 7.90%N; Found: 54.17%C: 5.98%H: 7.71%N.

EXAMPLE 6

3-{1-[Phenethyl]-4-piperidinyl}-1,2-benzisothiazole hydrobromide

A stirred mixture of 5.0 g of 3-(4-piperidinyl)-1,2-benzisothiazole, 4.60 g of phenethyl bromide, 7.95 g of potassium carbonate, 0.25 g of potassium iodide and 90 ml of dimethylformamide was heated at 60° for 20 hrs and stirred for 2½ days at ambient temperature. The reaction mixture was poured into water and extracted with ethyl acetate. The organic extracts were dried over anhydrous magnesium sulfate and the solvent was removed in vacuo to yield an oil. The oil was purified by elution column chromatography [silica gel (20:1); using 1% methanol in dichloromethane]. The eluate was evaporated and the residue was dissolved in ether and a saturated hydrogen bromide/ether solution was added dropwise to precipitate the salt. The salt was recrystallized from ether-ethanol 3.0 g (32%) of product, mp 233°–235°.

Analysis: Calculated for $C_{20}H_{22}N_2S.HBr$: 59.55%C: 5.46%H: 6.95%N; Found: 59.61%C: 5.75%H: 6.82%N.

EXAMPLE 7

3-(1-Benzoyloxy-4-piperidinyl)-1,2-benzisothiazole

A mixture of 5.23 g of 3-(4-piperidinyl-1,2-benzisothiazole, 6.0 g of benzoyl peroxide, 6.8 g of potassium carbonate and 100 ml of benzene was stirred at ambient temperature for 20 hrs. The reaction mixture was filtered and the filtrate was concentrated in vacuo to yield an oil. The oil was purified by elution column chromatography (silica gel (15:1)), ethyl acetate:hexane (40:60) as eluent. The eluent was evaporated to a solid. The solid was recrystallized 2 times from hexane to yield 5.0 g (61.0%) of product, mp 84°–85°.

Analysis: Calculated for $C_{19}H_{18}N_2O_2S$: 67.46%C: 5.33%H: 8.28%N; Found: 67.55%C: 5.46%H: 8.32%N.

EXAMPLE 8

3-[1-(6-Fluoro-1,2-benzisoxazole-3-propyl)-4-piperidinyl]-1,2-benzisothiazole hydrochloride A mixture of 1.6 g of 3-(4-piperidinyl)-1,2-benzisothiazole, 1.76 g of (3-chloropropyl)-6-fluoro-1,2-benzisoxazole, 1.2 g of potassium carbonate and 30 ml of dimethylformamide was stirred, under nitrogen, at 100° for 5 hrs. The reaction was poured in water and the water extracted with ethyl acetate. The ethyl acetate extract was washed with water, brine and dried over anhydrous magnesium sulfate. Evaporation of the solvent in vacuo yielded an oil. Chromatography (120 g of alumina) of the oil using ether as the eulant gave a solid, after evaporation of the solvent. The solid was treated with ether/hydrogen chloride to form a salt. Recrystallization of the salt from ethanol gave 1.1 g (35%) of product, mp 238°–240°.

Analysis: Calculated for $C_{22}H_{22}FN_3OS$ HCl: 61.17%C: 5.13%H: 9.73%N; Found: 61.37%C: 5.42%H: 9.74%N.

EXAMPLE 9

3-[1-(1,3-Dihydro-2-oxo-2H-benzimidazol-1-ylpropyl)-4-piperidinyl]-1,2-benzisothiazole A mixture of 2.2 g of 3-(4-piperidinyl)-1,2-benzisothiazole hydrochloride was converted to its free base. A mixture of the free base, 1.0 g of sodium carbonate, 1.8 g of 1-(3-chloropropyl)-1,3-dihydro-2H-benzimidazol-1-one and 60 ml of 2-methyl-4-pentanone was heated under reflux for 6 hrs, with stirring. After cooling, the mixture was poured into water and the aqueous mixture extracted with ethyl acetate. The extract was washed with water, dried over anhydrous magnesium sulfate, and the solvent removed in vacuo to yield an oil. The oil solidified on standing. After decanting some supernatant liquid, the solid was diluted with ether and collected. The solid was recrystallized twice from dimethylformamide-water to yield 1.1 g (33.3%) of product, mp 185°–187°.

Analysis: Calculated for $C_{22}H_{24}N_4OS$: 67.32%C: 6.16%H: 14.08%N; Found: 67.00%C: 6.13%H: 14.21%N.

EXAMPLE 10

3-{1-[4,4-bis-(4-Fluorophenyl)-1-butyl]-4-piperidinyl}-1,2-benzisothiazole hydrochloride A mixture of 5.0 g of 3-(4-piperidinyl)-1,2-benzisothiazole, 7.70 g of 4-chloro-1,1-bis(4-fluorophenyl)butane, 7.0 g of potassium carbonate, 0.25 g of potassium iodide and 120 ml of dimethylformamide was stirred at 90° for 8.0 hrs and overnight at ambient temperature. The reaction mixture was poured into water, extracted with ethyl acetate, washed with water, dried over anhydrous magnesium sulfate and the solvent was removed in vacuo to yield an oil. The product was purified by high-pressure liquid chromatography using dichloromethane:methanol (2%) as the eluent. The eluent was evaporated, the residue was dissolved in ether and a saturated hydrogen chloride/ether solution was added dropwise to yield a solid. The solid was recrystallized from ethyl acetate/ether to give 2.0 g (21%) of product, mp 198°–199°.

Analysis: Calculated for $C_{28}H_{28}F_2N_2S \cdot HCl$: 67.54%C; 5.83%H; 5.63%N; Found: 67.23%C; 5.48%H; 5.48%N.

EXAMPLE 11

3-{3-[4-(1,2-benzisothiazol-3-yl)piperidinyl]propyl}-2-methyl indole hydrochloride A stirred mixture of 5.0 g of 3-(4-piperidinyl)-1,2-benzisothiazole, 7.50 g of 2-methyl-3-(phenylsulfonylpropyl)indole, 15.0 g of potassium carbonate, 120 ml of dimethylformamide and 0.25 g of potassium iodide was heated to 90° for 8 hrs and allowed to stand overnight at ambient temperature. The reaction mixture was poured into water, dried over anhydrous magnesium sulfate and the solvent was removed in vacuo to yield an oil. The oil was purified by high-pressure liquid chromatography using dichloromethane:methanol (2%) as the eluent. The eluent was evaporated. The residue was dissolved in ether and saturated hydrogen chloride/ether solution was added dropwise to precipitate the salt. The salt was recrystallized 2 times from acetonitrile/ether to yield 2.0 g (30%) of product, mp 231°–232°.

Analysis: Calculated for $C_{24}H_{27}N_3S \cdot HCl$: 67.84%C; 6.60%H; 9.89%N; Found: 67.26%C; 6.54%H; 9.70%N.

I claim:

1. A method of treating psychoses comprising administering to a mammal in need of psychoses treatment a psychoses-treating, effective amount of a compound of the formula

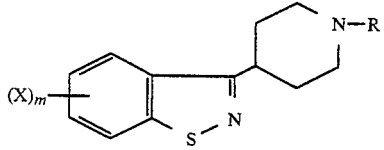

wherein R is hydrogen, loweralkyl, loweralkenyl, cycloalkylloweralkyl, phenylloweralkyl, hydroxy, diloweralkyaminoloweralkyl, cyano, cyanomethyl,

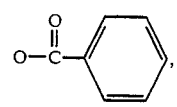

a group of the formula

wherein $R^1$ is hydrogen, loweralkyl or a group of the formula $OR^2$ wherein $R^2$ is phenyl or benzyl; a group of the formula

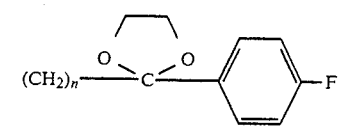

wherein n is 2 or 3; a group of the formula

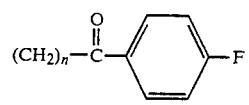

wherein n is 2 or 3; a group of the formula

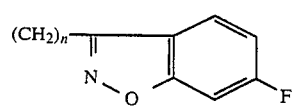

wherein n is 2 or 3; a group of the formula

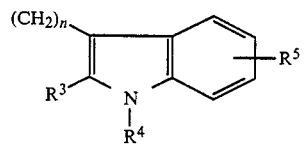

wherein $R^3$ and $R^4$ are each independently hydrogen or loweralkyl, $R_5$ is hydrogen, halogen or loweralkyl, and n is 2 or 3; a group of the formula

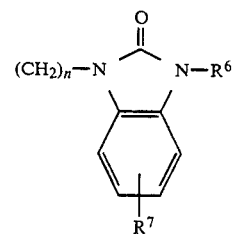

wherein $R^6$ is hydrogen or loweralkyl, $R^7$ is hydrogen, halogen or loweralkyl, and n is 2 or 3; or a group of the formula

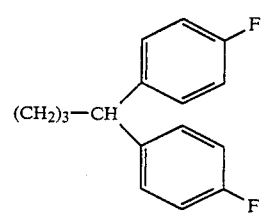

X is hydrogen, halogen, loweralkyl, loweralkoxy or hydroxy; and m is 1 or 2; the optical antipodes thereof; or pharmaceutically acceptable acid addition salts thereof.

2. A psychoses-treating composition comprising an inert psychoses-treating adjuvant and, as the active ingredient, an amount effective in treating psychoses of a compound of the formula

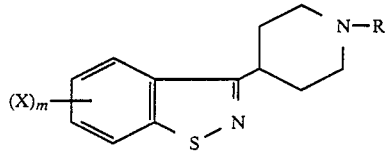

wherein R is hydrogen, loweralkyl, loweralkenyl, cycloalkylloweralkyl, phenylloweralkyl, hydroxy, diloweralkyaminoloweralkyl, cyano, cyanomethyl,

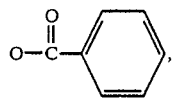

a group of the formula

wherein $R^1$ is hydrogen, loweralkyl or a group of the formula $OR^2$ wherein $R^2$ is phenyl or benzyl; a group of the formula

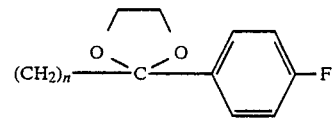

wherein n is 2 or 3; a group of the formula

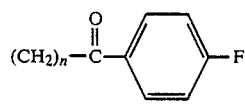

wherein n is 2 or 3; a group of the formula

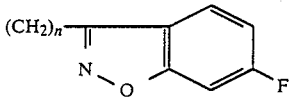

wherein n is 2 or 3; a group of the formula

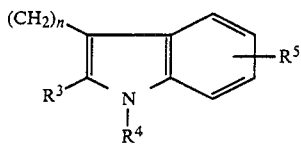

wherein $R^3$ and $R^4$ are each independently hydrogen or loweralkyl, $R_5$ is hydrogen, halogen or loweralkyl, and n is 2 or 3; a group of the formula

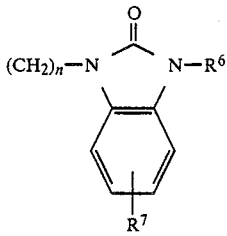

wherein $R^6$ is hydrogen or loweralkyl, $R^7$ is hydrogen, halogen or loweralkyl, and n is 2 or 3; or a group of the formula

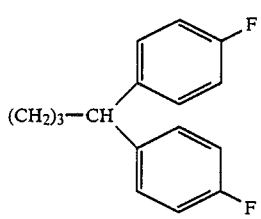

X is hydrogen, halogen, loweralkyl, loweralkoxy or hydroxy; and m is 1 or 2; the optical antipodes thereof; or pharmaceutically acceptable acid addition salts thereof.

* * * * *